United States Patent [19]

Leroux

[11] Patent Number: 4,559,181

[45] Date of Patent: Dec. 17, 1985

[54] HYDROXY-DIPHOSPHONIC ACID DERIVATIVES OF HIGHER CARBOXYLIC ACIDS

[75] Inventor: Yves Leroux, Paris, France

[73] Assignee: Minemet Rechreche, Trappes, France

[21] Appl. No.: 563,933

[22] Filed: Dec. 21, 1983

Related U.S. Application Data

[63] Continuation-in-part of Ser. No. 411,285, Aug. 25, 1982, abandoned.

[51] Int. Cl.⁴ .............................................. C07F 9/38
[52] U.S. Cl. ............................................. 260/502.4 A
[58] Field of Search ................................ 260/502.4 A

[56] References Cited

U.S. PATENT DOCUMENTS

| | | | |
|---|---|---|---|
| 3,366,677 | 1/1968 | Quimby | 260/502.4 A |
| 3,400,149 | 9/1968 | Quimby et al. | 260/502.4 A |
| 3,551,480 | 12/1970 | Germscheid et al. | 260/502.4 A |
| 3,855,284 | 12/1974 | Germscheid | 260/502.4 A |
| 4,060,546 | 11/1977 | Blaser et al. | 260/502.4 A |
| 4,316,877 | 2/1982 | Tonick et al. | 260/502.4 A |
| 4,332,736 | 1/1982 | Starner et al. | 260/502.4 A |

OTHER PUBLICATIONS

Prentice et al, "Interaction of Acylating Agents and Phosphorus (III) Sources", J.A.C.S., vol. 94, No. 17, Aug. 23, 1972, pp. 6119–6124.

*Primary Examiner*—J. E. Evans
*Attorney, Agent, or Firm*—Fleit, Jacobson, Cohn & Price

[57] ABSTRACT

A high efficiency process for producing hydroxy-diphosphonic acid derivatives of higher carboxylic acids comprising a first step of mixing a tri-valent phosphorous compound with the higher carboxylic acid in a molar ratio in the range of 13:12 to 18:12, and subsequently heating the reaction mixture to a temperature of 80° to 110° C. for about 3 to 20 hours.

In one embodiment, a subsequent solvolysis step is employed wherein the product resulting from the heating step is heated with a solvent having a hydroxyl function.

27 Claims, 1 Drawing Figure

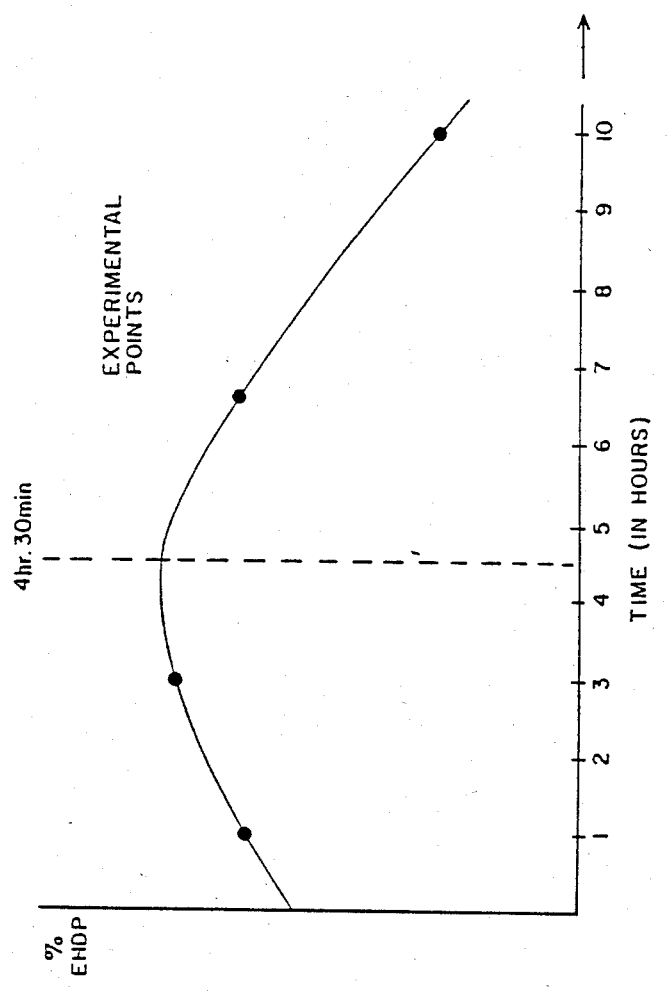

HYDROXY-DIPHOSPHONIC ACID DERIVATIVES OF HIGHER CARBOXYLIC ACIDS

CROSS REFERENCE TO RELATED APPLICATIONS

This application is a continuation-in-part of U.S. patent application Ser. No. 411,285, filed August 25, 1982, now abandoned.

BACKGROUND OF THE INVENTION

1. Field of the Invention

The present invention is directed to a process for the production of hydroxy-diphosphonic acid derivatives of higher carboxylic acids.

It has more specifically as an aim the production of said derivatives of carboxylic acids slightly soluble in water, that is carboxylic acids having more than 13 carbon atoms.

This new process is more specially adapted to produce hydroxy-diphosphonic derivatives of carboxylic acids having more than 15 carbon atoms.

2. Description of the Prior Art

The technique for producing hydroxy-diphosphonic acid derivatives of lower carboxylic acids has been known for many years, especially for the derivatives of acetic acid.

Nevertheless, the yields of such known processes are relatively low and these yields drop even more when one attempts to hydroxy-diphosphonate carboxylic acids having more than 13 carbons.

The HENKEL company, in its Belgian Pat. No. 619,600, describes a process which produces diphosphonated acids containing large quantities of the starting compounds, at relatively low yields in relation to the phosphonating reagent added (on the order of 30% of phosphorus converted into hydroxy-diphosphonic acid). This has been verified by using this technique for the conversion of fatty acids having a relatively high number of carbons. In this regard, one may refer to the comparative experiment below which reproduces for stearic acid the conditions described in this Belgian patent (corresponding to the U.S. Pat. No. 4,060,546).

More recently, the ALLIED CORPORATION has obtained U.S. Pat. No. 4,316,877 where the technique of the preceding patent is utilized for the manufacture of extracting compositions. Nevertheless, as will be seen in the comparative example which follows, this process does not improve markedly that described in the HENKEL patents.

The compounds produced by diphosphonating carboxylic acids are of growing interest, especially those compounds having a sufficiently high number of carbons to be liposoluble while being very hydrophobic, for the extraction by ion exchange of different metals, especially uranium, from highly acidic mediums or very chelating mediums, such as is described in European Patent Application No. 81,400633,4.

In general, it is not acceptable to have low yields vis-a-vis the reagents used for any organic product whose cost governs the use in industrial processes.

In addition, in the patents mentioned above, one by-product of the reaction, phosphorous acid, is not reusable since non-used during the reaction. This is the reason why research which has been carried out leading to the present invention has concentrated on the use of this by-product in as high a quantity as possible.

SUMMARY OF THE INVENTION

Based on the above, one of the objects of the present invention is to provide a process for the production of hydroxy-diphosphonated derivatives of higher carboxylic acids in substantially higher yields relative to the tri-valent phosphorous reactants than the techniques described previously.

Another object of the present invention is to provide a process for the production of hydroxy-diphosphonated derivatives of higher carboxylic acids, the by-products of which might be easily recyclable.

Another object of the present invention is to provide a process of the preceding type which permits one to obtain either the corresponding diphosphonic tetracid, or esters whose average composition corresponds to a diacid diester.

Yet another object of the present invention is to provide a process for purifying the tetracid.

The objects, as well as others which will appear in the following pages, are obtained by the new process of production of hydroxy-diphosphonic acid derivatives of higher carboxylic acids, said process comprising:

(a) mixing said higher carboxylic acid with a tri-valent phosphorous reagent selected from tri-halogenides of phosphorous, phosphorous acid and their mixtures, in the absence of water, wherein the molar ratio of the tri-valent phosphorous reagent to the corresponding carboxylic acid is in the range of about 13:12 to 18:12; and (b) heating the resulting mixture to a temperature in the range of about 80° to 110° C. for a period of about 3 to 20 hours.

BRIEF DESCRIPTION OF THE DRAWING

The Figure is a graph demonstrating the relationship between the amount of product and the duration of heating.

DESCRIPTION OF THE PREFERRED EMBODIMENT

In fact, in a totally surprising manner, and contrary to the idea which one skilled in the art might have, using a molar relationship higher in phosphorous reagent permits one to improve considerably the yield based on phosphorus. This seems to go contrary to the law of mass action as well as the intuitive idea which one has; thus, any explanation requires the use of concepts of intermediary reactions which for the moment are not well known.

Therefore, one critical aspect of the present invention is the discovery that increasing the molar proportion of tri-valent phosphorous reactant beyond that taught by the prior art results in a substantially higher percentage of the phosphorous being combined with the carboxylic acid reactant in the form of the desired hydroxy-diphosphonic acid derivative.

Concerning the temperature of stage (a), one should note that the reaction is exothermic at the beginning, probably because of the reactions of dehydration which lead to the elimination of water from the reaction medium and to the dehydration of the carboxylic group. This explanation is nevertheless not exhaustive.

It is desirable to maintain a temperature lower than 110° C. and preferably upper than 80° C. Nevertheless, when one does not use a diluent, as will be explained later on, it is difficult to obtain such temperatures when the melting temperature of the corresponding carboxylic acid is higher than the above values. It is desirable, for the reactions which are supposed to occur at the beginning of the mixture to work, that the carboxylic acid be melted. The temperature is preferably chosen between the melting point of the corresponding carboxylic acid and 110° C.

One good means of regulating the temperature is in the speed of addition of the phosphorous tri-halogenide. Thus, the speed of addition of the tri-halogenide of phosphorus is chosen so that the temperature of the reaction mixture does not exceed 110° C.

An optimal value for the molar ratio of tri-valent phosphorous reagent to the carboxylic acid is in the range of about 15:12 (±10%).

According to a preferred method of the invention, the tri-valent phosphorous reagent comprises a tri-halogenide of phosphorus and phosphorous acid; the molar relationship ($PX_3/H_3PO_3$; x=halogen) between the tri-halogenide of phosphorus and the phosphorous acid is in the range of about 0.3 to 1 and 0.6 to one, preferably between about 0.4 for 1 and 0.5 to 1.

As another embodiment of this invention, it is possible to use to produce phosphorous acid "in situ" by making the tri-halogenide of phosphorus used react with water rather than add the phosphorous acid directly. This method of carrying out the process has the drawback of not permitting recycling of the phosphorous acid. Nevertheless, it is appropriate to observe that the partial use of this method of operation permits the use of reagents which include a little water, the decomposition of the tri-halogenide of phosphorus to give some phosphorous acid permitting an accelerated dehydration of the compounds.

One can thereby use some phosphorous acid and/or carboxylic acid containing a slight amount of water, on the condition of knowing the quantity of water contained and adjusting the amounts of phosphorous acid and the tri-halogenides used.

For economic reasons, the tri-halogenide of phosphorus which is preferred is phosphorous trichloride.

During the present study, it has been demonstrated that it is desirable to add a polar aprotic diluent which favors considerably the reaction, while resolving the possible difficulties linked to the higher melting point of the carboxylic acids to be transformed into hydroxy-diphosphonic compounds.

Among the polar aprotic diluents, the best are the branched and cyclic linear ethers having a boiling point in the range of about 80° to 150° C. which permits a good regulation of the temperature of the reaction mixture, and, preferably, the sulphones, with the best diluents being the substituted or nonsubstituted ones.

The heating of stage (b) takes place in general one half-hour to one hour after mixing of said carboxylic acid and the tri-valent phosphorous reagent, and during this period the temperature of the reaction mixture is that determined either by the exothermicity of the reaction, or by the melting point of the carboxylic acid.

The preferred duration of heating depends on the heating temperature chosen, this depending, as has been explained previously, on the fusion temperature of the carboxylic acid. The higher the temperature, the shorter the duration of heating; and, reciprocally, the lower the temperature, the longer the heating period.

Experts in the field may be guided on the one hand by the classic consideration that an increase of 10° C. corresponds to a doubling of the kinetic energy and, on the other hand, by the fact that at 90° C. a satisfactory duration is on the order of 10 to 12 hours.

The reaction mixture obtained following the heating contains not only the diphosphonic acid derivative in a low proportion, but also contains a number of compounds from condensation which it is preferred to solvolyse in order to free the hydroxy-diphosphonic acid derivatives contained therein.

Thus, one embodiment of the process according to the present invention includes, in addition, a stage of solvolysis, as follows:

(c) solvolysis of said reaction mixture by heating with a solvent having a hydroxyl function.

Solvolysis may be carried out either by alcohols, in which case one will obtain an ester, or a mixture of esters, or by water, in which case one will obtain a hydroxy-diphosphonic tetracid.

When one wishes to obtain tetracid, the heating is carried out at reflux in the presence of a halohydric acid for 1 to 6 hours, with the concentration in halohydric acid being between 2 and 6 N. The volume relationship between said reaction mixture obtained after stage (b) and the aqueous halohydric acid is between 1:1 and 4:1.

When the solvolysis is an alcoholysis, the solvolysis is carried out at a temperature between 110° and 140° C., preferably between 110° and 120° C.

When the boiling point of the alcohol is lower than 110° C., solvolysis is carried out under pressure, for example in a sealed tube, and the use of metallic containers should be avoided.

Solvolysis may also be carried out in a diluent. It then suffices to choose a diluent inert to both the reaction mixture issuing from stage (b) and the alcohol used. One can use, for example, heavy ethers or even alcohol itself. The amount of alcohol put into the process with the reaction mixture from stage (b) is an amount greater than the stoichiometric amount necessary for the esterification of the two acid functions of the potential hydroxy-diphosphonic compound produced in the course of the reaction, preferably an amount higher than the sum of the stoichiometric amount necessary for the esterification of the two acid functions of the potential hydroxy-diphosphonic compound produced during the reaction and the stoichiometric amount necessary for the esterification of the residual carboxylic acid. Most preferably an amount at least two times the sum of the stoichiometric amount necessary for the esterification of the two acid functions of the potential hydroxy-diphosphonic compound produced during the reaction and the stoichiometric amount necessary for the esterification of the residual carboxylic acid is used.

The examples which follow and which have no exhaustive character have as their aim to permit those skilled in the art to determine easily the operating conditions to be used in each specific case.

EXAMPLE 1. COMPARATIVE EXAMPLE

This example reproduces the teaching of the Belgian Pat. No. 619,600, corresponding to the U.S. Pat. No. 4,060,546, by applying the technique used by BLASER for lauric acid to stearic acid (example 5 of the Belgian patent and example 7 of the U.S. patent).

The entire technique has been summarized and it is not useful to repeat it here, the only difference consisting in the replacement of the lauric acid by stearic acid and the total amount of the reaction mixture, since the reaction was carried out in laboratory conditions on amounts 100 times smaller, i.e. 17.06 grams of stearic acid, 5.49 grams of phosphorous trichloride and 1.08 gram of water.

In order to better compare this example with the operating conditions of the present invention, one can point out that the molar ratio between tri-valent phosphorous reagent and the stearic acid is 0.67; however the relationship between phosphorous acid and phosphorous trichloride.is 1. One thus finds very different conditions from the stoichimetric conditions of the present invention.

One recovers, as indicated in the BLASER patent, a sodium salt which contains almost all of the phosphorous originally used (more than 85%).

Nevertheless, the tracings of nuclear magnetic resonance (NMR) relative to phosphorus 31 demonstrate that this sodium salt corresponds not to any pure hydroxy-diphosphonic acid but to a mixture of complexes in which the pure hydroxy-diphosphonic acid occurs only in a small proportion and shows some resemblance to tracings obtained from reaction mixtures issuing from stage (b), i.e., before solvolysis.

This salt was then subjected to a hydrolysis according to the techniques described below.

After adding 4 N chlorhydric acid, in an amount equal to twice the weight of the sodium salt, and heating under reflux at a temperature of about 120°–130° C., the reaction mixture is refluxed for approximately 8 hours, then left to cool again. After cooling, the phase is submitted to an extraction by ether. Ether phase and the residual aqueous phase were separately recovered, then the two phases subjected to an NMR examination of the phosphorus 31. The ether phase contained essentially hydroxy-diphosphonic acid, however the aqueous phase contained only phosphorous acid. Calculation of the amount of phosphorus in the two phases demonstrates that only 0.36 gram of phosphorus are combined as hydroxydiphosphonic acid, a yield of less than 30% based on the starting amount of 1.23 grams of phosphorus.

This yield is much lower than the yields obtained by the practice of the present invention.

EXAMPLE 2. COMPARATIVE EXAMPLE

This example follows, as much as possible, the conditions described in example 1 of the U.S. Pat. No. 4,316,877 (M.A. TUNICK, columns 5 and 6) by using stearic acid as the starting carboxylic acid.

The conditions described are duplicated completely except that the temperature of the mixture is 80° C. instead of 50° C. In fact, it is impossible to obtain a homogeneous mixture with stearic acid at a temperature of 50° C. It is necessary to raise it to 80° C.

The conditions of lines 12 to 20 of column 6 were selected, which favors, according to TUNICK, the formation of the hydroxy-diphosphonic acid derivative. Thus, following the addition, the solution was heated to 110° C. for 16 hours. Upon cooling, a white solid was obtained.

Nevertheless, contrary to what is indicated in lines 15 and 16 of TUNICK, the addition of water to this solid had no notable effect on the NMR of phosphorus 31 after 10 hours without heating. There was nothing or almost nothing in the aqueous phase, contrary to what is described in the U.S. Pat. No. 4,316,877, and the solid put into organic solution (tetra-hydrofurane) showed three peaks, one of which is very important: 15.88, 14.60, and 14.13 ppm in relation to orthophosphoric acid. Thus the product is not hydroxy-diphosphonic acid, it is a mixture of complexes. On the other hand, when this solid was treated, according to an option of TUNICK, with water as described earlier, and the entirety evaporated under vacuum (by Rotavapor) at 90° C. for 5 hours, the NMR spectrum of phosphorus 31 of the organic product, insoluble in water, shows that only one-third of the mixture is the hydroxy-diphosphonic acid derivative of stearic acid (20.06 ppm in relation to orthophosphoric acid). One finds markedly the same proportion as that obtained in the earlier example 1, which is not very surprising because the operating conditions are very similar to those used by BLAZER.

In summary, if the U.S. Pat. No. 4,316,877 seems to describe correctly the reaction with the products in $C_9$ and $C_{12}$, the expression of line 26 which declares that the product in $C_{18}$ is obtained "in similar manner" appears erroneous. In fact, on the one hand, the solubilities in the aqueous phase are not at all those which the experimenter has found (none of the products obtained is water soluble, contrary to what is said); on the other hand, the operating conditions are not able to be carried out since one is constrained to heat at 80° C. instead of 50° C., otherwise the reaction would practically not take place. Finally, extrapolation of the data of TUNICK, demonstrates returns which are quite a bit lower than those of the present invention.

EXAMPLE 3 SYNTHESIS ACCORDING TO THE INVENTION

In a flask equipped with a cooler and a vessel with a brome glass, 200 grams of stearic acid, 48 grams of anhydrous phosphorous acid and 60 ml of sulfolane were mixed. Slowly, by means of the brome glass vessel, 65 grams of phosphorous trichloride was added while the temperature was permitted to rise to about 80° C. The reaction mixture was then heated under agitation for 9 hours at of about 95° to 100° C., and then 600 grams of 4 N chlorhydric acid was added for 8 hours. After purification of the product (cf. example 4), 84 grams of stearic acid and 135 grams of pure hydroxy-diphosphonic acid of stearic acid were recovered.

| Analysis: | C = | 50.15% | Calculated: | C = | 50.17% |
|---|---|---|---|---|---|
| | H = | 8.77% | | H = | 9.27% |
| | P = | 14.41% | | P = | 14.4% |

This figure of 135 grams corresponds to a yield, based on the stearic acid which reacted, calculated by the yield in relation to the non-recovered stearic acid, i.e. that which disappeared during the reaction and the purification, of 80%. This figure nevertheless is a minimum because the technique of purification, which will be described in the following example, involves non-negligable losses of hydroxy-diphosphonic acid derivative.

Concerning phosphorous, 32.79 grams of phosphorus were used in the course of the reaction. 135 grams of hydroxy-diphosphonic acid derivative correspond to 19.1 g of phosphorus in the form of the hydroxy-diphosphonic acid derivative, which corresponds to a return of fixation of phosphorus of 60%, much higher than that seen in the two earlier prior art examples. And yet, this return is a minimum because a part of the hydroxy-diphosphonic acid derivative was lost during purification.

Additionally, taking into account the fact that the process according to the present invention uses phosphorous acid, the unreacted phosphorus, which is found almost entirely in the form of phosphorous acid, can easily be recycled and used for a subsequent hydroxy-diphosphonation.

EXAMPLE 4: PURIFICATION OF HYDROXYDIPHOSPHONIC ACID BASED ON THE HYDROLYSATE

One uses the property of stearic acid of being insoluble in water but soluble in carbon tetrachloride, chloroform, ether and THF, while hydroxy-diphosphonic acid derivatives of higher carboxylic acids are insoluble in chloroform and soluble in THF.

The organic phase of the hydrolysate is thus separated from the aqueous phase, washed in water, then put into solution in the minimal quantity of THF or of THF plus ether. One then adds progressively chloroform. One obtains a pale white-yellow solid which one dries in an oven under vacuum. This powder whitens in air progressively. It should be noted that there is no melting at all of this product which decomposes before melting.

EXAMPLE 5: ALCOHOLYSIS OF THE REACTION MIXTURE

The reaction mixture as described above is submitted to an evaporation in a vacuum to evacuate the residual volatile materials. It is then redissolved in n-heptyl alcohol in excess (200 cc of n-heptyl alcohol for 100 grams of reaction mixture after removal of the volatile materials). The mixture is heated at reflux (120° C.) and gives an ester of hydroxy-diphosphonic acid whose phosphorous and carbon analysis corresponds to a diester, although the NMR spectrum of phosphorus 31 resembles the product obtained by esterification of pure stearic acid HDP and of ethyl orthoformate.

EXAMPLE 6

In the same conditions as those described in Example 3, but under the following stoichiometric relations: 12 $RCOOH + 10H_3PO_3 + 5PCl_3$, napthenic acid was reacted (product sold by SHELL). A very good return (41%) of HDP naphthenoic acid in relation to the naphthenic acid put in initially was recovered.

EXAMPLE 7

Using the same conditions as before, a study of the influence of the duration of heating as a function of the molecular weight was conducted. The table below summarizes the optimal results obtained.

| RCOOH | M | Duration of heating |
|---|---|---|
| $CH_3COOH$ | 60 | 1 h at RT then 2–3 h at 85–90° C. |
| $(C_2H_5)CHCOOH$ | 116 | 1 h at RT then 5–7 h at 85–90° C. |
| $CH_3(CH_2)_5COOH$ | 130 | 1 h at RT then 6–8 h at 85–90° C. |
| Naphthenic Acid | 310 | 1 h at RT then 10–12 h at 85–90° C. |

M: molecular weight
RT: room temperature

The results demonstrated that the heating could be longer or at a slightly higher temperature, but that did not give better returns after hydrolysis of the condensate and the hydrolysis took more time to be completed.

EXAMPLE 8: EXPERIMENTAL STUDY OF HYDROLYSIS

Water is not very effective for hydrolysis of the condensate. The best conditions have been studied. It is best to use an acid hydrolysis, using a relatively concentrated halohydric acid. Kinetic studies have shown that the best conditions depended on the hydrophilous character of the carboxylic acids used. When the carboxylic acids used are water-soluble, the best conditions seem to be a temperature of reflux of 120°–130° C. in the presence of 4 to 6 N chlorhydric acid.

Concerning the duration of heating, the optimum seems to be, for water-soluble acids, around 4 ½ hours. See the Figure.

For liposoluble acids, i.e. for acids whose number of carbon atoms is higher than 15, this optimum seems to be around 8 hours.

I claim:

1. A process for production of hydroxy-diphosphonic acid derivatives of higher carboxylic acids comprising:
   (a) mixing said carboxylic acid and a tri-valent phosphorous reagent selected from the group comprising the tri-haloginides of phosphorous and mixtures of tri-haloginides and phosphorous acid, to form a reaction mixture, wherein the molar ratio of said tri-valent phosphorous reagent and said carboxylic acid is in the range of about 13:12 to 18:12; and
   (b) heating said reaction mixture of (a) to a temperature in the range of about 80° to 110° C. for a time in the range of about 3 to 20 hours.

2. The process according to claim 1, wherein the reaction mixture contains no water.

3. The process according to claim 1, wherein said higher carboxylic acid is a carboxylic acid containing more than 13 carbon atoms.

4. The process according to claim 1, wherein said carboxylic acid contains more than 15 carbon atoms.

5. Process according to claim 1, wherein during the period of the mixing of said carboxylic acid with said tri-valent phosphorous reagent, the temperature is maintained between the melting point of said corresponding carboxylic acid and 110° C.

6. Process according to claim 1, wherein said mixing of said carboxylic acid with said tri-valent phosphorus comprises adding progressively said tri-valent phosphorous reagent to said carboxylic acid, the speed of addition of said tri-valent phosphorous reagent being such that the temperature of the reaction mixture does not exceed 110° C.

7. Process according to claim 1, wherein the molar ratio of said tri-valent phosphorous reagent to said carboxylic acid is about 15:12.

8. Process according to claim 1, wherein the tri-valent phosphorous reagent comprises a mixture of trihalogens of phosphorus and phosphorous acid having a molar ratio in the range of about 0.3:1 to 0.6 to 1.

9. Process according to claim 8, wherein said molar ratio is in the range of about 0.4:1 to 0.5:1.

10. Process according to claim 1, wherein said phosphorous acid is produced "in situ" by hydrolysis of a phosphorous trihalogenide, the phosphorous trihalogenide being introduced at the same time as the stoichiometric amount of water necessary for the hydrolysis.

11. Process according to claim 1, wherein said reaction mixture further contains a polar aprotic diluent.

12. Process according to claim 11, wherein said polar aprotic diluent is a sulphone.

13. Process according to claim 11, wherein said polar aprotic diluent is a substitued sulpholane.

14. Process according to claim 11, wherein said polar aprotic diluent is a sulpholane.

15. Process according to claim 11, wherein said polar aprotic diluent is an ether selected from the group consisting of linear, branched and cyclic ethers having a boiling point in the range of 80° to 150° C.

16. Process according to claim 1, wherein said heating step (b) is effected one-half hour to one hour after said carboxylic acid and said tri-valent phosphorous reagent have been mixed, during said one-half hour to one hour the temperature of said reaction mixture is that determined by the exothermicity of the reaction.

17. Process according to claim 1 and further including the following step:
(c) solvolysis of the reaction mixture from step (b) by heating with a solvent having a hydroxyl function.

18. Process according to claim 17, wherein said solvent having a hydroxyl function is water and the heating is carried out by reflux in the presence of a halohydric acid for one to six hours, the concentration of said halohydric acid in the range of 2 to 6 N.

19. Process according to claim 18, wherein the concentration of said halohydric acid is in the range of 4 to 5 N.

20. Process according to claim 18, wherein the volume ratio between said reaction mixture obtained after stage (b) and said aqueous halohydric acid is in the range of 1:1 to 4:1.

21. Process according to claim 17, wherein said solvent having a hydroxyl function is an alcohol selected from the group consisting of linear, branched, or cyclic alcohols and by the fact that the solvolysis is carried out by heating at a temperature between about 110° and 140° C. for a period of about 6 to 15 hours.

22. Process according to claim 21, wherein the heating is carried out at a temperature between about 120° and 140° C.

23. Process according to claim 21, characterized by the fact that when said alcohols have a boiling point lower than 100° C., the solvolysis is carried out under pressure.

24. Process according to claim 21, wherein the solvolysis is carried out in a diluent.

25. Process according to claim 21, wherein the amount of alcohol put into reaction with the reaction mixture from stage (b) is a quantity larger than the stoichiometric quantity necessary for the esterification of the two acid functions of the potential hydroxy-diphosphonic compound produced during the reaction.

26. Process according to claim 24, wherein the amount of alcohol put into reaction with the reaction mixture from stage (b) is an amount greater than the sum of the stoichiometric amount required for the esterification of the two acid functions of the potential hydroxy-diphosphonic compound produced in the course of the reaction and the stoichiometric amount necessary for the esterification of the residual carboxylic acid.

27. Process according to claim 25, wherein the amount of alcohol put into reaction with the reaction mixture from stage (b) is an amount higher by a factor of two than the sum of the stoichiometric amount necessary for the esterification of the two acid functions of the potential hydroxy-diphosphonic compound produced in the course of the reaction and the stoichiometric amount necessary for the esterification of the residual carboxylic acid.

* * * * *

UNITED STATES PATENT AND TRADEMARK OFFICE
CERTIFICATE OF CORRECTION

PATENT NO. : 4,559,181
DATED : December 17, 1985
INVENTOR(S) : Yves LEROUX

It is certified that error appears in the above-identified patent and that said Letters Patent is hereby corrected as shown below:

TITLE PAGE, LEFT COLUMN:

Delete "[73] Assignee: Minemet Rechreche, Trappes, France"

and insert therefor:

--[73] Assignee: Minemet Recherche, Trappes, France--.

Signed and Sealed this

Thirtieth Day of August, 1988

Attest:

DONALD J. QUIGG

*Attesting Officer*

*Commissioner of Patents and Trademarks*